US00PP23386P3

(12) United States Plant Patent
de Does

(10) Patent No.: US PP23,386 P3
(45) Date of Patent: Feb. 12, 2013

(54) **VARIETY OF *LANTANA* PLANT NAMED 'NEBLAN5151'**

(50) Latin Name: *Lantana camara*
Varietal Denomination: NEBLAN5151

(75) Inventor: Hans de Does, Muenster (DE)

(73) Assignee: Volmary GmbH, Muenster (DE)

( * ) Notice: Subject to any disclaimer, the term of this patent is extended or adjusted under 35 U.S.C. 154(b) by 0 days.

(21) Appl. No.: 13/135,185

(22) Filed: Jun. 28, 2011

(65) Prior Publication Data

US 2012/0180173 P1 Jul. 12, 2012

Related U.S. Application Data

(60) Provisional application No. 61/460,911, filed on Jan. 10, 2011.

(51) Int. Cl.
*A01H 5/00* (2006.01)

(52) U.S. Cl. ..... Plt./227

(58) Field of Classification Search ..... Plt./227
See application file for complete search history.

*Primary Examiner* — Kent L Bell
(74) *Attorney, Agent, or Firm* — The Webb Law Firm

(57) ABSTRACT

'NEBLAN5151' is a new variety of *lantana* plant having a compact growth habit and white and lemon bicolored flowers.

2 Drawing Sheets

Botanical classification: *Lantana camara.*
Varietal denomination: 'NEBLAN5151'.

BACKGROUND OF THE INVENTION

The present invention comprises a new and distinct cultivar of *Lantana camara* known by the varietal name 'NEBLAN5151'. The new variety was discovered in Muenster, Germany in the Summer of 2007. The new variety is a result of a cross of proprietary and unpatented *lantana* plants. The purpose of the breeding program was to develop a *lantana* variety that was early flowering, with a compact growth habit and low seed setting. The new variety is similar in plant habit and flower size to its female parent, but differs in flower color. 'NEBLAN5151' is similar in plant habit to its male parent, but differs in flower color. Further, the new variety is similar in plant habit and early flowering time to *lantana* variety 'Lucky White' (unpatented), but differs in flower color, as 'Lucky White' has all white flowers, and the present variety has white flowers with lemon-colored centers. The new variety was first asexually reproduced by cuttings in September of 2007 in Muenster, Germany. The new variety has been trial and field tested and has been found to retain its distinctive characteristics and remain true to type through successive propagations.

The following characteristics have been repeatedly observed and are determined to be unique characteristics that distinguish 'NEBLAN5151' as a new and distinct cultivar from others known to the breeder:

1) Very compact plant habit;
2) Good branching with short internodes;
3) Early flowering time that is 2 weeks earlier than *lantana* standards such as 'Goldsonne' (unpatented); and
4) Small to medium-sized bicolored flowers (bright lemon and white).

DESCRIPTION OF THE DRAWINGS

The following photographic drawings illustrate the new variety, with the color being as nearly true as is possible with color illustrations of this type.

DESCRIPTION OF THE PLANT

Figure 1:
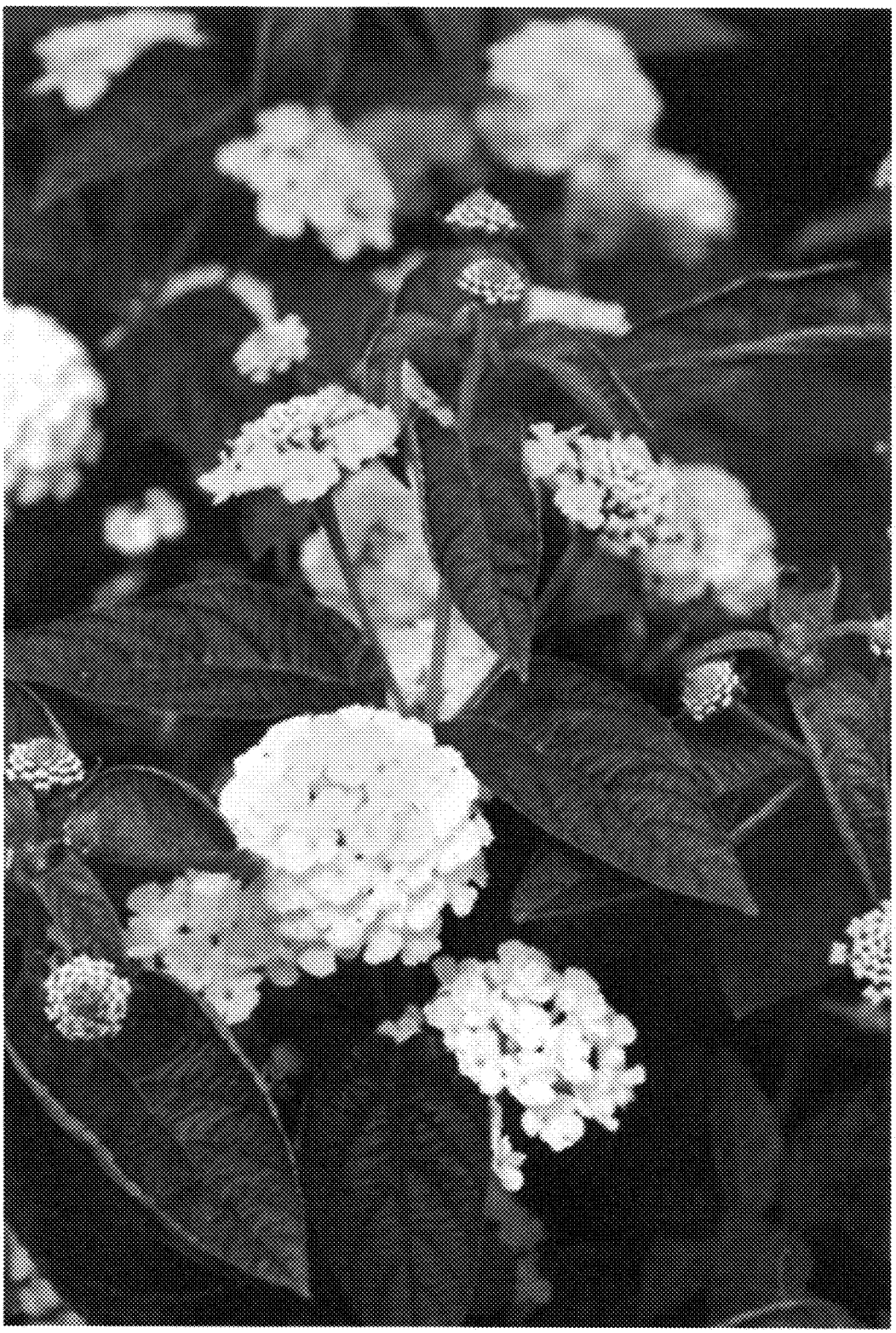
FIG. 1 is a photograph of the new variety.
Figure 2:
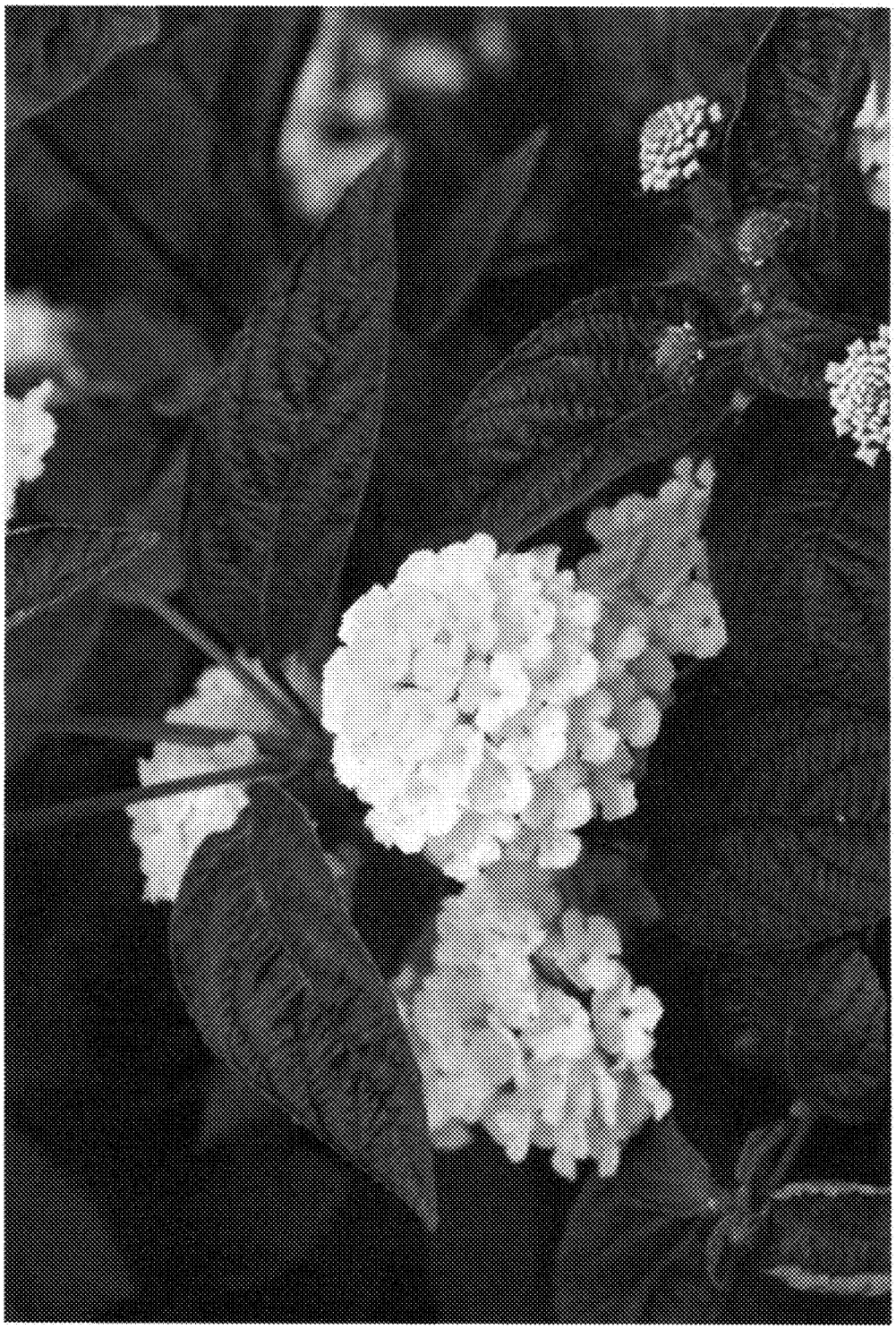
FIG. 2 is a close up photograph of the flowers of the new variety.

The following detailed description sets forth the characteristics of the new cultivar. The data which defines these characteristics were collected by asexual reproductions carried out in Muenster, Germany. The new variety was grown in a greenhouse under natural light at temperatures of 16-18° C. Color readings were taken under natural light. The new variety was 15 weeks old and grown in a 12 cm container when described. Color references are primarily to The R.H.S. Colour Chart of The Royal Horticultural Society of London.

PLANT

Time to initiate roots: About 10 days at about 20° C.
Time to develop roots: About 20 days at about 18-20° C.
Time to produce a finished flowering plant from a rooted cutting: About 10 weeks in a 12 cm container.
Rooting habit: Shallow, with good branching.
Form: Mounded.
Height from media surface to top of foliage: 25 cm.
Height from media surface to top of flowers: 25 cm.
Plant diameter: 30 cm.
Vigor: Strong.
Branching habit: Medium to strong.
Lateral branch:
*Average number.*—4.
*Length.*—5 cm.
*Diameter.*—0.3-0.5 cm.
*Internode length.*—5 cm.
*Strength.*—Upright and strong.
*Texture.*—Hispid.
*Color.*—144A.
Foliage:
*Arrangement.*—Single and opposite.
*Length.*—6-7 cm.

*Width*.—3.5-4 cm.
*Shape of leaf*.—Lanceolate.
*Apex*.—Acute.
*Base*.—Round and pointed.
*Margin*.—Serrate.
*Texture* (*both surfaces*).—Rough; pilary; hispid.
*Aspect*.—Horizontal.
*Pubescence* (*both surfaces*).—Light.
*Color*.—Young leaves: Upper surface: Between 141A and 144A. Lower surface: 141A. Mature leaves: Upper surface: 136A. Lower surface: 137A.
*Petiole*.—Length: 5-6 cm. Diameter: 0.2 cm. Texture: Pilary; hispid. Color: 144A.
*Veins*.—Venation type: Feather. Color: Upper surface: 146C. Lower surface: 146C.

FLOWERS

Flower arrangement: Hemispherical axial umbels with 20-30 single flowers.
Flower habit: Trumpet-like.
Natural flowering season: Spring until later summer (April until frost).
Fragrance: Lemon balm.
Inflorescence:
*Height*.—2 cm.
*Diameter*.—3-4 cm.
Buds (described 1-2 days before opening):
*Length*.—0.6 cm.
*Diameter*.—0.2 cm.
*Shape*.—Trumpet-like.
*Color*.—14A.
Flowers:
*Normal flowering season*.—From spring until frost.
*Average flower longevity on the plant*.—About 2 weeks.
*Appearance*.—Small balls made up of 40-50 flowers.
*Diameter*.—1-1.2 cm.
*Height*.—1.4 cm.
*Shape*.—Trumpet-like.
*Throat diameter*.—0.1-0.2 cm.
*Tube*.—Length: 1.2-1.3 cm. Diameter: 0.2 cm.
Corolla:
*Arrangement*.—Base is fused to the tube.
*Petals*.—Color: Upper surface (when opening): 4A. Upper surface (fully opened): 4A. Lower surface (when opening): 12A. Lower surface (fully opened): 4D. Shape: Truncate. Length: 15-19 mm. Width: 4-5 mm. Apex: Truncate and slightly unrelated. Base: Fused to tube. Margin: Smooth. Number per whorl: 5. Texture: Smooth.
*Throat color*.—Young flower: 7D. Mature flower: 4D.
*Tube color*.—Young flower: 7D. Mature flower: 4D.
Calyx:
*Appearance*.—Fused to small tube.
*Length*.—0.3 cm.
*Diameter*.—0.1 cm.
*Sepals*.—Average number: 5. Apex: Pointy. Base: Fused to tube. Texture: Pubescence present. Margin: Lightly crenate with pubescence present. Color (both surfaces): 145A.
Umbrella stem (peduncles):
*Length*.—4-5 cm.
*Diameter*.—0.2 cm.
*Texture*.—Pubescence present.
*Color*.—144A.
Pedicels:
*Length*.—2.5-4.5 cm.
*Diameter*.—10-15 mm.
*Color*.—144A.
Disease/pest resistance: None observed to date.
Temperature tolerance: Medium.
Drought tolerance: Medium.

REPRODUCTIVE ORGANS

Stamens:
*Number* (*per flower*).—5.
*Filament*.—Length: 0.1 cm. Color: 141D.
*Anthers*.—Shape: Didynamous, bithecous. Length: 0.1 cm. Color: 14A.
*Pollen*.—Color: 12A. Amount: Medium.
Pistils:
*Number* (*per flower*).—1.
*Length*.—0.3-0.4 cm.
*Style*.—Length: 0.3 cm. Color: 4D.
*Stigma*.—Shape: Obliquely subcapitate. Length: 2 mm.
*Ovaries*.—Position: Superior. Length: 0.1 cm. Width: 0.1 cm. Color: 141D.
Seeds:
*Number*.—1.
*Length*.—0.5-0.6 cm.
*Diameter*.—0.4 cm.
*Color*.—160B.

I claim:

1. A new and distinct variety of *lantana* plant named 'NEBLAN5151' as is herein described and illustrated.

* * * * *